United States Patent
Weiner

(10) Patent No.: US 10,327,778 B2
(45) Date of Patent: Jun. 25, 2019

(54) STENT WITH BALLOON FOR REPAIR OF ANASTOMOSIS SURGERY LEAKS

(71) Applicant: BOSTON SCIENTIFIC SCIMED, INC., Maple Grove, MN (US)

(72) Inventor: Jason Weiner, Grafton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 174 days.

(21) Appl. No.: 14/192,578

(22) Filed: Feb. 27, 2014

(65) Prior Publication Data

US 2014/0243950 A1 Aug. 28, 2014

Related U.S. Application Data

(60) Provisional application No. 61/770,403, filed on Feb. 28, 2013.

(51) Int. Cl.
*A61B 17/11* (2006.01)
*A61F 5/00* (2006.01)
(Continued)

(52) U.S. Cl.
CPC ............ *A61B 17/1114* (2013.01); *A61F 2/04* (2013.01); *A61F 2/064* (2013.01); *A61F 2/07* (2013.01);
(Continued)

(58) Field of Classification Search
CPC .... A61F 2/064; A61F 2/07; A61F 2/04; A61F 2/06; A61F 2/82; A61F 2002/072; A61F 2002/075; A61F 2002/077; A61F 2002/823; A61F 2250/0039; A61F 5/003; A61F 5/0036; A61F 5/0079; A61F 2/86; A61F 2/88; A61F 2/90; A61F 2/91; A61F 2/24; A61F 2/2409; A61F 2/2418; A61F 2002/821; A61F 2002/825; A61B 17/11; A61B 17/1114; A61B 2017/1107; A61B 2017/1132

See application file for complete search history.

(56) References Cited

U.S. PATENT DOCUMENTS

| | | | | |
|---|---|---|---|---|
| 4,800,819 A | * | 1/1989 | Frey | B61D 3/14 105/238.1 |
| 5,084,061 A | | 1/1992 | Gau et al. | |

(Continued)

FOREIGN PATENT DOCUMENTS

| | | |
|---|---|---|
| EP | 2143387 A1 | 1/2010 |
| FR | 2834199 A1 | 7/2003 |

(Continued)

OTHER PUBLICATIONS

International Search Report, International Application No. PCT/US2014/019119, Boston Scientific Scimed, Inc., dated May 26, 2014 (6 pgs.).

*Primary Examiner* — Christopher L Templeton
(74) *Attorney, Agent, or Firm* — Seager, Tufte & Wickhem, LLP

(57) ABSTRACT

A stent for repairing post-anastomosis surgery leaks is described. The stent includes an elongated tube having a flared proximal end and a flared distal end, and an intermediate region disposed between those two ends. An inflatable balloon is disposed about the intermediate region. In addition, the elongated tube is coated with a coating.

16 Claims, 8 Drawing Sheets

(51) Int. Cl.
   *A61M 29/02*    (2006.01)
   *A61F 2/958*    (2013.01)
   *A61F 2/04*     (2013.01)
   *A61F 2/06*     (2013.01)
   *A61F 2/07*     (2013.01)

(52) U.S. Cl.
   CPC ............ *A61F 2/958* (2013.01); *A61F 5/0036* (2013.01); *A61F 5/0079* (2013.01); *A61F 2002/045* (2013.01); *A61F 2250/0003* (2013.01); *A61F 2250/0039* (2013.01)

(56) References Cited

U.S. PATENT DOCUMENTS

| | | | |
|---|---|---|---|
| 5,238,004 A | 8/1993 | Sahatjian et al. | |
| 5,308,326 A * | 5/1994 | Zimmon | A61B 5/02152 604/103.1 |
| 5,330,528 A * | 7/1994 | Lazim | A61F 2/07 606/194 |
| 5,534,024 A * | 7/1996 | Rogers | A61F 2/07 606/195 |
| 5,662,713 A * | 9/1997 | Andersen | A61F 2/90 128/898 |
| 5,665,117 A * | 9/1997 | Rhodes | A61F 2/07 606/192 |
| 5,707,355 A * | 1/1998 | Zimmon | A61B 17/12036 604/104 |
| 5,725,572 A * | 3/1998 | Lam | A61B 19/54 600/3 |
| 5,741,333 A * | 4/1998 | Frid | A61F 2/90 623/1.18 |
| 5,843,160 A * | 12/1998 | Rhodes | A61F 2/07 606/194 |
| 5,922,019 A * | 7/1999 | Hankh | A61F 2/90 606/198 |
| 6,096,021 A * | 8/2000 | Helm | A61B 17/12113 604/103.01 |
| 6,508,803 B1 | 1/2003 | Horikawa et al. | |
| 6,675,809 B2 | 1/2004 | Stack et al. | |
| 6,827,735 B2 * | 12/2004 | Greenberg | A61B 17/12109 623/1.25 |
| 7,150,758 B2 * | 12/2006 | Kari | A61F 2/06 623/1.25 |
| 7,608,086 B2 | 10/2009 | Tanaka et al. | |
| 7,666,220 B2 * | 2/2010 | Evans | A61B 17/12118 623/1.25 |
| 7,674,271 B2 | 3/2010 | Bjerken | |
| 7,695,446 B2 | 4/2010 | Levine et al. | |
| 7,758,535 B2 | 7/2010 | Levine et al. | |
| 8,118,856 B2 * | 2/2012 | Schreck | A61F 2/07 623/1.13 |
| 2001/0021872 A1 * | 9/2001 | Bailey | A61F 2/2418 623/1.24 |
| 2001/0023369 A1 * | 9/2001 | Chobotov | A61F 2/07 623/1.11 |
| 2002/0032486 A1 | 3/2002 | Lazarovitz et al. | |
| 2002/0165572 A1 * | 11/2002 | Saadat | A61B 17/12022 606/194 |
| 2003/0023303 A1 * | 1/2003 | Palmaz | A61F 2/2418 623/2.18 |
| 2003/0069647 A1 * | 4/2003 | Desmond, III | A61F 2/94 623/23.7 |
| 2003/0209835 A1 * | 11/2003 | Chun | A61F 2/2412 264/339 |
| 2003/0212450 A1 * | 11/2003 | Schlick | A61F 2/07 623/1.15 |
| 2004/0039452 A1 | 2/2004 | Bessler | |
| 2004/0249439 A1 * | 12/2004 | Richter | A61F 2/86 623/1.15 |
| 2005/0060029 A1 * | 3/2005 | Le | A61F 2/2418 623/2.11 |
| 2005/0085900 A1 * | 4/2005 | Case | A61F 2/2418 623/1.24 |
| 2006/0015190 A1 | 1/2006 | Robertson | |
| 2006/0074481 A1 | 4/2006 | Vardi et al. | |
| 2006/0116752 A1 * | 6/2006 | Norton | A61F 2/90 623/1.34 |
| 2006/0184238 A1 * | 8/2006 | Kaufmann | A61F 2/90 623/1.53 |
| 2006/0206198 A1 * | 9/2006 | Churchwell | A61B 17/12022 623/1.25 |
| 2006/0212112 A1 * | 9/2006 | Evans | A61F 2/07 623/1.25 |
| 2006/0276887 A1 * | 12/2006 | Brady | A61F 2/90 623/1.53 |
| 2006/0292206 A1 * | 12/2006 | Kim | A61B 17/12022 424/443 |
| 2007/0100435 A1 * | 5/2007 | Case | A61F 2/2418 623/1.24 |
| 2007/0179590 A1 * | 8/2007 | Lu | A61F 2/07 623/1.16 |
| 2007/0282453 A1 * | 12/2007 | Weitzner | A61F 2/04 623/23.7 |
| 2007/0293937 A1 * | 12/2007 | Biggs | A61L 27/34 623/1.13 |
| 2008/0097513 A1 * | 4/2008 | Kaji | A61B 17/12099 606/192 |
| 2008/0195137 A1 * | 8/2008 | Alleyne | A61M 25/10 606/195 |
| 2009/0012544 A1 | 1/2009 | Thompson et al. | |
| 2009/0192588 A1 | 7/2009 | Shin et al. | |
| 2009/0287145 A1 | 11/2009 | Cragg et al. | |
| 2010/0100105 A1 | 4/2010 | Bates et al. | |
| 2011/0060398 A1 * | 3/2011 | Tupil | A61F 2/07 623/1.15 |
| 2011/0071613 A1 * | 3/2011 | Wood | A61F 2/88 623/1.11 |
| 2011/0307070 A1 | 12/2011 | Clerc et al. | |
| 2011/0319980 A1 * | 12/2011 | Ryan | A61F 2/07 623/1.16 |
| 2012/0004676 A1 | 1/2012 | Vargas | |
| 2012/0041538 A1 * | 2/2012 | White | A61F 2/885 623/1.12 |
| 2012/0203264 A1 * | 8/2012 | Karwa | A61B 17/12118 606/194 |
| 2012/0232361 A1 | 9/2012 | Birk | |
| 2013/0110253 A1 * | 5/2013 | Gill | A61F 2/04 623/23.68 |
| 2013/0304196 A1 * | 11/2013 | Kelly | A61F 2/2475 623/1.25 |
| 2014/0364959 A1 * | 12/2014 | Attar | A61F 5/0076 623/23.7 |

FOREIGN PATENT DOCUMENTS

| | | |
|---|---|---|
| WO | 9719653 A1 | 6/1997 |
| WO | 20090132309 A1 | 10/2009 |
| WO | 20090149294 A1 | 12/2009 |
| WO | 2011137318 A2 | 11/2011 |

* cited by examiner

STENT WITH BALLOON FOR REPAIR OF ANASTOMOSIS SURGERY LEAKS

CROSS-REFERENCE TO RELATED APPLICATIONS

This application claims priority under 35 U.S.C. § 119 to U.S. Provisional Application Ser. No. 61/770,403, filed Feb. 28, 2013, the entirety of which is incorporated herein by reference.

TECHNICAL FIELD

The present disclosure relates generally to methods and apparatuses for repairing post-anastomosis surgery leaks (for example, bariatric surgery). More particularly, the disclosure relates to different configurations and methods of manufacture and use of a stent.

BACKGROUND

Obesity is a medical condition in which excess body fat in an individual has accumulated to the extent that it may have an adverse effect on the individual's health, leading to reduced life expectancy and/or increased health problems. A measurement index, known as the Body Mass Index (BMI) is calculated based on the weight and height of an individual. Generally, an individual having a BMI above 30 kg/m$^2$ is considered obese. Obesity is most commonly caused by a number of factors that may include consumption of excessive dietary calories, lack of physical activity, medication side effects, genetic susceptibility, and/or through a combination of these factors. Typically, an obese individual encounters an increased susceptibility to diseases such as type 2 diabetes, certain types of cancer, osteoarthritis, severe heart conditions, breathing problems, etc., further fueling the development of an undesirable lifestyle, which may include issues of body fatigue, weariness, depression, sleep disorder, and the like. Such conditions may result in adverse effects on the individual's physical and mental health, reducing the individual's participation in physical, social, and other day-to-day activities, thus reducing life expectancy.

On average, obesity reduces life expectancy by six to seven years, and in light of the above noted health conditions, obesity has become a leading preventable cause of death worldwide. With an ever-increasing noted prevalence in adults, children, and elders, many categorize it among the most serious of public health problems. The WHO estimated in 2005 that at least 400 million adults (9.8% worldwide) were obese. Further, according to a report submitted by CDC (Centers for Disease Control and Prevention), 34% of adults and 17% of children in the United States were obese in 2007-2008. More specifically, in the United States alone, more than 10 million people are reportedly obese, out of which, obesity has been estimated to cause up to 365,000 deaths per year, while approximately 150,000 people undergo obesity related treatments every year.

Bariatric (or weight loss) surgery is one such commonly performed obesity related treatment, which is commonly applied to handle cases of severe obesity. Severe obesity defines individuals having a BMI greater than 40 kg/m$^2$. The most common bariatric surgery is referred to as Roux-en-Y (depicted in FIG. 1), in which a small gastric pouch (approximately 25% of the stomach's size) and an alimentary limb (Roux limb) are created and is operably anastomosed to each other, and thereafter, to the patient's jejunum, bypassing one part of the small intestine. Other bariatric surgeries include sleeve gastrectomy and/or biliopancreatic diversion with duodenal switch (depicted in FIG. 2), in which, the stomach size is reduced by about 80% of the actual size through surgical procedures. This forms a thin sleeve like stomach, which provides reduced capacity for food intake. Such surgery bypasses the majority of the intestine by connecting the end portion of the intestine to the duodenum near the stomach (biliopancreatic diversion).

These weight-loss surgeries are observed to be effective, but carry along a list of health related risks that range from malnutrition, vitamin deficiencies, etc. Long-term studies however propose that weight loss experienced by the patient in such surgeries is significant. Further, improvements such as recovery from diabetes, improvement in cardiovascular health, and a reduction in mortality of 23% to 40%, have been observed as well.

Reportedly, postoperative gastric leaks occur in about 2% to 3% of bariatric surgeries, but the actual number may be higher because of underreporting. Gastric leaks mostly occur at the portion where the gastric pouch is stapled or surgically joined to a connective tissue, and at the gastrojejunal anastomosis, which establishes the surgical connection between the stomach and the jejunum. Additionally, gastric leaks have also been reported at the junction between the gastric pouch and the esophagus, commonly referred generally to as the Z-line. Such leaks are one of the most dreaded complications that may accompany a bariatric surgery, and in general, is one of the major causes of increased morbidity and mortality rates in obese patients undergoing such treatments. Treatments for medical conditions such as these commonly include site drainage with parenteral nutrition and bowel rest, other endoscopic methods, re-operation, etc., all of which are known to include drawbacks.

SUMMARY

This disclosure is directed to several alternative designs, materials, and methods of manufacturing medical device structures and assemblies, for preventing leaks after an anastomosis surgery.

Accordingly, one illustrative embodiment is a stent for repairing post-anastomosis surgery leaks. The stent includes an elongated tube, a coating applied over the elongated tube, and an inflatable balloon, disposed around the stent's intermediate region. The elongated tube has a flared proximal end and a flared distal end, having the stent's intermediate region configured between those two ends.

Another illustrative embodiment of the present disclosure describes a stent for repairing post-anastomosis surgery leaks. The stent includes an elongated tube with a flared proximal end region, a flared distal end region, and an intermediate region, which extends between the proximal end region and the distal end region. Further, a polymeric coating is applied over the elongated tube, which in turn includes an inflatable balloon configured and secured about its midway at the intermediate region. Additionally, the inflatable balloon includes an inflation valve.

Certain embodiments of the present disclosure describe a method of repairing post-anastomosis surgery leaks. The method includes providing a stent, which has an elongated tube structured with flared proximal and distal ends, accompanied by an intermediate region configured between those two ends. The elongated tube includes a coating, and has an inflatable balloon arranged about the intermediate region. Further, the method includes the step of mounting the stent onto an elongated device, and advancing the stent and elongated device through a corresponding body lumen.

Subsequently, the step of positioning the stent adjacent to a post-anastomosis surgery leak is performed, which is followed by expanding the stent in that positioned state. There, an operator or user may inflate the inflatable balloon before finally removing the elongated device from the body lumen.

The above summary of exemplary embodiments is not intended to describe each disclosed embodiment or every implementation of the present disclosure.

BRIEF DESCRIPTION OF THE DRAWINGS

The invention may be more completely understood in consideration of the following detailed description of various embodiments in connection with the accompanying drawings, in which.

Figure 1:
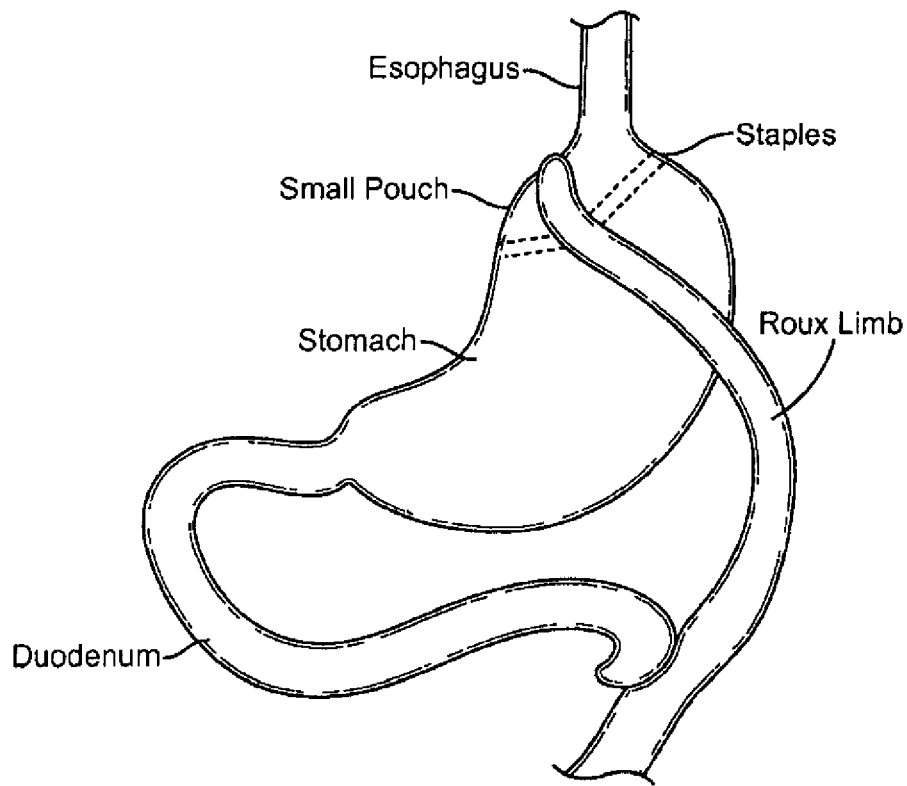
FIG. 1 is a schematic view of portions of an alimentary canal after a Roux-en-Y procedure.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may be indicative as including numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

Although some suitable dimensions, ranges, and/or values pertaining to various components, features and/or specifications are disclosed, one of the skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

For purposes of this disclosure, "proximal" refers to the end closer to the device operator during use, and "distal" refers to the end further from the device operator during use.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with one embodiment, it should be understood that such feature, structure, or characteristic may also be used connection with other embodiments whether or not explicitly described unless cleared stated to the contrary.

Roux-en-Y bariatric surgery (shown in FIG. 1), carried out to treat obese patients, commonly includes the surgical cutting, removal, and re-connection of tissue, in and around, and of the stomach. Tissue re-connections generally includes at least two layers of tissue being brought together to be sutured or surgically stapled and joined, forming a stapled or stapling line. Such joining may require time to heal. During the course of healing, leakage of any consumed food, gastric juices, etc., occurring at the stapling line or elsewhere may prove fatal.

Similarly, sleeve gastrectomy, also applied in treating obesity, and interchangeably referred to as biliopancreatic diversion with duodenal switch (see FIG. 2), also includes the removal of a substantial portion of the stomach. Conceptually, this type of surgery may differ from the Roux-en-Y, but involving procedures such as surgical cutting, suturing, stapling etc., may remain considerably similar to those of Roux-en-Y. Both these types of surgeries are prone to conditions of post-anastomosis leakage. In the present disclosure, a stent is disclosed and described that may prevent and repairs such leaks. While the devices and methods described herein are discussed relative to the repair of post-bariatric surgery leaks, it is contemplated that the devices and methods may be used in other treatment locations and/or applications for the treatment of leaks resulting from any anastomosis surgery. For example, the devices and methods described herein may be used between body lumens and/or between body lumens and organs anywhere in the body.

Figure 3:
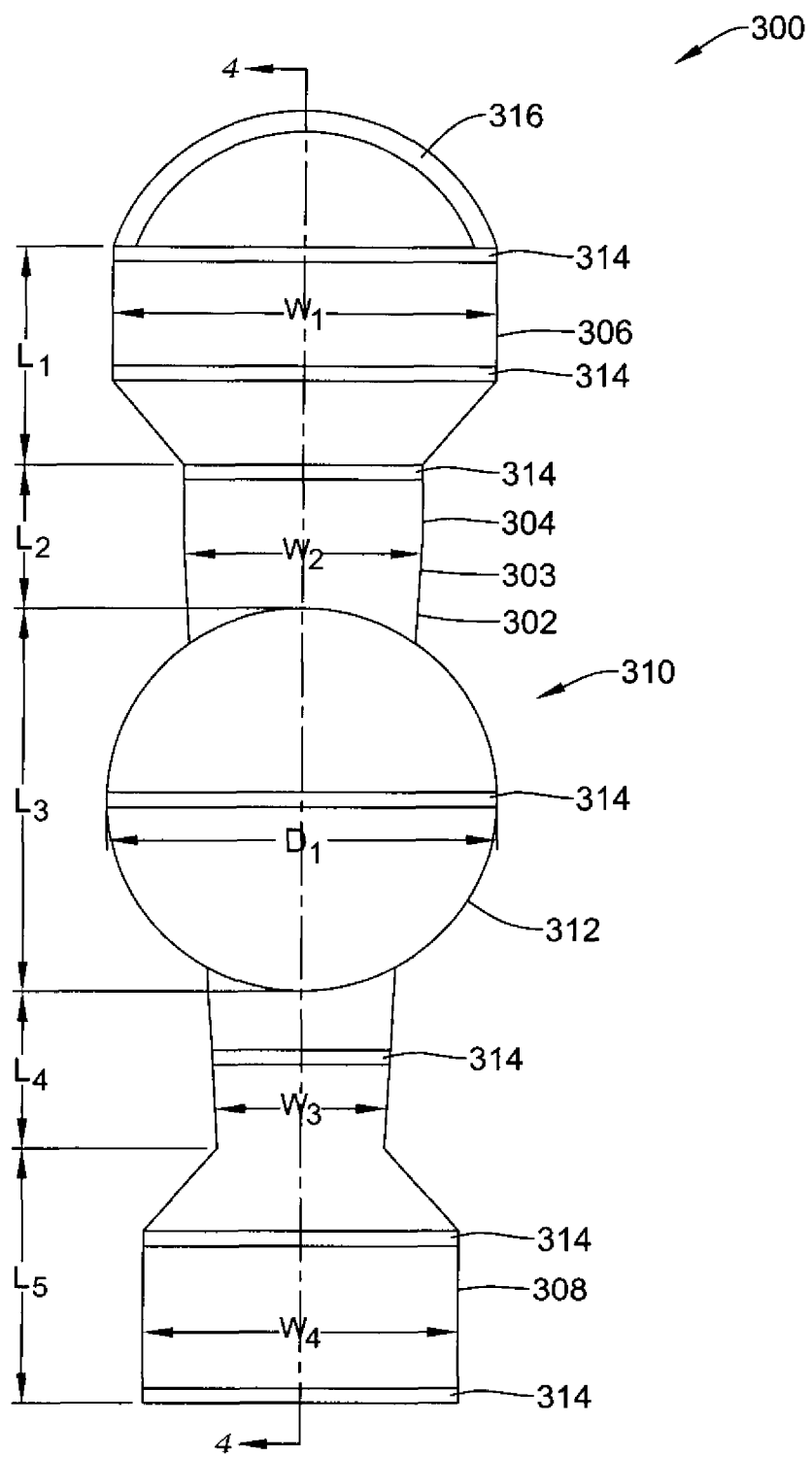
FIG. 3 is a side view of an illustrative stent.
Figure 4:
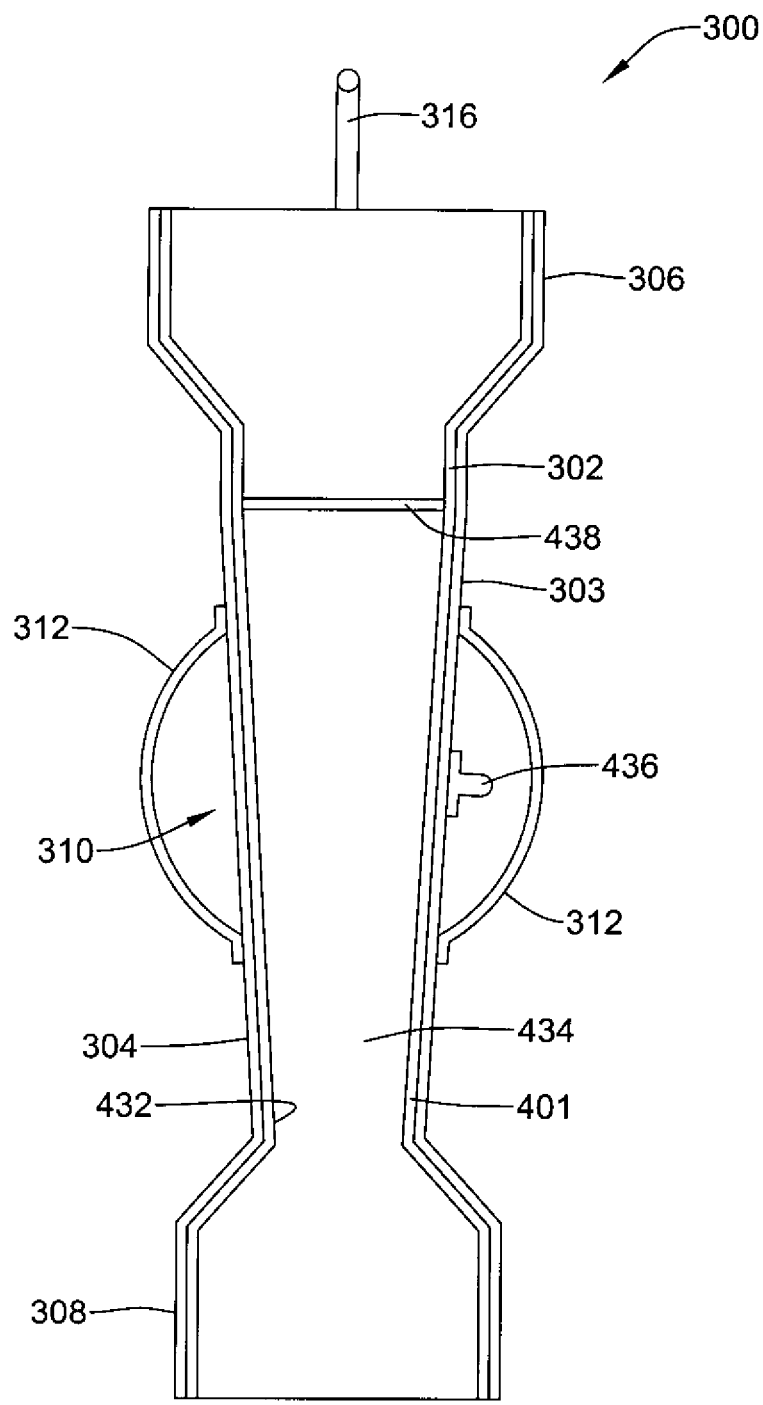
FIG. 4 is a schematic cross-sectional view of the illustrative stent of FIG. 3.

Accordingly, FIG. 3 and FIG. 4 illustrate an exemplary stent 300 configured to be arranged and positioned within the gastric pouch or the small pouch after a Roux-en-Y bariatric surgery (see FIG. 1). FIG. 4 is a cross-section of the illustrative stent 300 of FIG. 3, taken at line 4-4. The arrangement is configured to temporarily prevent leakage of fluids, food, etc., traveling through the esophagus, into the small pouch once the surgery is over. More specifically, the proposed arrangement of the stent 300 may effectively prevent any food or gastric juices from reaching the stapling line, established during the surgery, and leaking thereof. Such leakage may be generally classified as post-anastomosis surgery leaks, as noted above. The stent 300 may be placed adjacent the stapling line where leaks are most likely to occur. Being in that position, the stent 300 may provide physical isolation to the stapling line, offering resistance to any form of leakage at that region. Effectively, such isolation may enable the stapling line to be repaired and healed over a period.

More descriptively, the stent 300 may be placed substantially entirely within the small pouch, created during the bariatric surgery (see FIG. 1), such that proximal and distal portions (discussed in more detail below) of the stent 300, may prevent the food or liquid, etc., from passing between the stent 300 and the enteral wall. Moreover, the stent 300 may be removed once the surgical connections, established during the bariatric surgery, have healed and a corrective tissue connection is established. A detailed description of the structure and functioning of the stent 300 has been described in the forthcoming disclosure.

The stent 300 may include an elongated tubular stent frame 302, which may be entirely, substantially or partially, covered with a polymeric covering or coating, referred hereinafter as coating 304. More particularly, the coating 304 may be disposed over an outer surface 401 (see FIG. 4) of the stent frame 302, forming an outer polymeric layer thereof. At either end, the stent 300 may include a flared proximal end region and a flared distal end region, hereinafter referred to as flared proximal end 306 and flared distal end 308, respectively, between which, an elongated tubular section 303 may be disposed. Further, the stent frame 302 may include an intermediate region 310, which may include an expandable middle segment 312. The expandable middle segment 312 may prevent distal/proximal displacement and/or migration of the stent 300, once the stent 300 is positioned and expanded.

In further detail, the stent frame 302 may be generally cylindrical in shape, although this is not required, substantially flexible, and sized appropriately for a convenient accommodation within the esophagus, small pouch, and the Roux limb. More particularly, when deployed in position, the flared proximal end 306, with an exemplary length L1, may rest substantially within the esophagus, the flared distal end 308, with an exemplary length L5, may rest within the Roux limb, while the expandable middle segment 312, with an exemplary length L3, may rest within the small pouch. The flared proximal end 306 and the flared distal end 308 may be configured to contact the corresponding body lumens to prevent passage of food or liquid between the stent 300 and the corresponding lumen wall. It is contemplated that various shapes, sizes and designs of the stent frame 302 may be constructed depending on the size and geometry of the cavities where the stent 300 has to be placed.

The stent frame 302 may have a woven structure, fabricated from a number of filaments. In some embodiments, the stent frame 302 may be braided with one filament. In other embodiments, the stent frame 302 may be braided with several filaments, as is found, for example, in the Wall-Flex®, WALLSTENT®, and Polyflex® stents, made and distributed by Boston Scientific. In another embodiment, the stent frame 302 may be knitted, such as the Ultraflex™ stents made by Boston Scientific. In yet another embodiment, the stent frame 302 may be of a knotted type, such the Precision Colonic™ stents made by Boston Scientific Scimed, Inc. In still another embodiment, the stent frame 302 may be laser cut, such as the EPIC™ stents made by Boston Scientific.

It is contemplated that the stent frame 302 can be made from a number of different materials such as, but not limited to, metals, metal alloys, shape memory alloys and/or polymers, as desired, enabling the stent 300 to be expanded into shape when accurately positioned within the body. In some instances, the material may be selected to enable the stent 300 to be removed with relative ease as well. For example, the stent frame 302 can be formed from alloys such as, but not limited to, nitinol and Elgiloy®. Depending the on material selected for construction, the stent 300 may be self-expanding. In some embodiments, fibers may be used to make the stent frame 302, which may be cored fibers, for example, having an outer shell made of nitinol having a platinum core. It is further contemplated the stent frame 302 may be formed from polymers including, but not limited to, polyethylene terephthalate (PET).

The coating 304 disposed on the outer surface 401 (see FIG. 4) of the stent frame 302, may be resistant to degradation. Additionally, the coating 304 may provide the structure of the stent 300 with an adequate ability to occlude leaks, preventing food and liquids from seeping through the open structure of the stent frame 302 and into the small pouch, when positioned and expanded. This may restrict food particles, etc., from undesirably passing through the "meshed structure" of the stent frame 302, which may occur in the absence of the coating 304. Further, the coating 304 may be applied throughout the structure of stent 300, and may be configured to effectively accommodate the stent's bends and flexures that may occur during the stent's transfer and deployment. To this end, the polymer may be made of a material that swells and/or the polymer may be coated with an agent that swells in situ. Additionally, the coating 304 may provide protection to the stent 300 from tissue ingrowth as well, which may otherwise complicate stent removal once the stapling line has healed. For example, the coating 304 may prevent tissue from growing around and thus attaching itself to the open framework of the stent frame 302.

The coating 304 may be composed of a biocompatible material and may accordingly be chemically stable as it may be exposed to tissue, blood vessels, and other internal organs of the human body, thus limiting harmful reactions when employed. In some embodiments, the coating 304 can be silicone, styrene isoprene butadiene (SIBS), expanded polytetrafluoroethylene (ePTFE), or polyurethane, although additional materials may be used as desired.

The coating 304 may be applied to the stent frame 302 through a number of various methods, such as, but not limited to dipping, spraying, sandwiching, heat shrinking, or electro-spinning. In some instances, methods of applying the coating 304 may include inserting the stent frame 302 into the interior of a mold conformed to the exterior shape of the stent 300. Thereafter, adding a suitable coating solution to the interior of the mold may be performed. Subsequently, rotating and tilting the mold about a center axis is carried out to substantially wrap the stent frame 302 with the coating solution. Finally, removing the coated stent 300 from the mold is executed. Other related and appropriate techniques to coat the stent frame 302 may be well known to someone in the art.

Optionally, an inner surface 432 of the stent frame 302 may be coated as well, forming an inner polymeric layer (not explicitly shown). The coating 304 may thus form an inner polymeric layer and an outer polymeric layer, with the stent 300 forming an intermediate layer, in-between those layers. In some instances, the inner and outer polymeric layers may contact one another, such as through the struts, braiding, or framework of the stent frame 302. In other instances, the outer polymeric layer of the coating 304 may permeate the stent frame 302 to create a smooth surface on the inner stent wall 432. When so provided, the inner polymeric layer may be applied simultaneously with the coating 304 during the stent's manufacture, although this is not required. In some instances, an inner coating layer may be applied separately from the outer coating 304. An inner coating may provide a smooth and non-restrictive passage for food and liquid passing through an inner lumen 434 of the stent 300.

The flared proximal end 306 and flared distal end 308, when in position, may prevent leakage of any food or liquid, etc., into the small pouch. Such sealing may be enabled by sealing the gaps between those ends 306, 308, and the enteral lumen walls. Disposed in a distal region of the esophagus, the flared proximal end 306 may expand along the circumference of the esophagus. The expanding structure may be such that the flared proximal end 306 may conically diverge out of the elongated tubular section 303. In some embodiments, the stent frame 302 has a larger cross sectional area at the flared proximal end 306 than the cross section at the elongated tubular section 303. In one embodiment, the flared proximal end 306 may have a length $L_1$ that ranges from approximately 18 to 22 millimeters (mm) and a width $W_1$ that ranges from approximately 28 to 32 mm at its widest portion. However, these ranges are merely exemplary. It is contemplated the width and length of each section may be determined by the desired application and/or placement within the body.

Similarly, the structure at the distal end of the stent 300, that includes the flared distal end 308, may be substantially similar in shape and size to the flared proximal end 306. In some embodiments, the flared distal end 308 may have a different size and shape depending on the size and geometry of the cavity within which it is being placed. Both the flared proximal end 306 and the flared distal end 308 thus form conically enlarged protrusions at their respective ends. In some embodiments, the shape, design, and size, may vary and may include variations such as U-shaped flares, etc., that may be needed depending on surgical and/or anatomical requirements. Alternatively, the flared ends 306 and 308 may have an open shape, such as a bowl shape, truncated cone, a saucer, etc. It is further contemplated that flared ends 306, 308 may be formed from inflatable balloons configured to conform to the size and shape of the vessel wall. In one embodiment, the flared distal end 308 may have a length $L_5$ that ranges from approximately 18 to 22 mm in length and a width $W_4$ that ranges from approximately 20 to 24 mm at its widest portion. However, these ranges are merely exemplary. It is contemplated the width and length of each section may be determined by the desired application and/or placement within the body.

When positioned and deployed, the stent 300 can be displaced due to factors that may include flexures and bends of the stomach, esophagus, organs in the vicinity, etc., occurring because of physical activity of the patient, and the like. In most cases, such displacements occur at the either ends of the stent 300, which may be referred to as the stent's proximal and distal migration. Such migration may inadvertently result in the creation of gaps between the stent 300 and the abutting inner walls of the adjacent organs, causing food or liquids to pass into the small pouch through those gaps. Notably, such leakage may restrict appropriate treatment to the stapling line, and in some cases, may even cause fatalities, as noted earlier.

To counter such conditions of stent migration, the stent 300 may include an expandable middle segment 312. The expandable middle segment 312 may extend 360° around the elongated tubular section 303, although this is not required. In some embodiments, the expandable middle segment 312 may extend less than 360° around the elongated tubular section 303. The expandable middle segment 312 may be disposed and secured at the intermediate region 310, and may be positioned within the small pouch until the stapling line is healed. Such an arrangement may help prevent the stent's migration. Moreover, the expandable middle segment 312 may also prevent stagnation and accumulation of food or liquid in the small pouch by filling the small pouch almost entirely.

In some embodiments, the expandable middle segment 312 may be formed from an inflatable balloon. The inflatable balloon 312 may include mechanisms and/or measures to allow a passage of air, saline, or other inflation fluid for performing functions of balloon inflation and deflation, as will be discussed in more detail below. In some instances, the inflatable balloon 312 may include, but is not limited to, a substantially spherical shape with a cylindrical hole in the center structured for the elongated tube's disposal therethrough. In some instances, the inflatable balloon 312 may be formed from a compliant, low pressure material, such as, but not limited to, silicone, synthetic polyisoprene, or latex. In other instances, the inflatable balloon 312 may be formed from a high pressure material, such as, but not limited to, polyethylene terephthalate (PET), nylon, polyethylene (PE), polyurethane, or flexible polyvinyl chloride (PVC).

Once the stent 300 is positioned within the small pouch, during deployment, the expandable middle segment 312 may be expanded to its desired shape and size. In some embodiments, the expandable middle segment 312 may have a diameter $D_1$ of approximately 39 mm resulting in an expandable middle segment 312 that may fill a gastric pouch having a volume of approximately 30 milliliters. In other embodiments, the expandable middle segment 312 may have a diameter $D_1$ of approximately 31 mm resulting in an expandable middle segment 312 that may fill a gastric pouch having a volume of approximately 15 milliliters. However, these are just examples. It is contemplated the diameter of the expandable middle segment 312 may be any size desired as determined by the desired application and/or placement within the body. For example, the diameter of the expandable middle segment 312 may be less than 31 mm or greater than 39 mm as desired. In some instances, the inflatable balloon 312 may be disposed over a length $L_3$ of the elongated tubular section 303. The length $L_3$ of the tubular section 303 may be determined by the size of the balloon 312. In some instances, the length $L_3$ may be approximately 38-42 mm.

One or more radiopaque marker bands 314 may be employed to positively position and expand the expandable middle segment 312 within the small pouch. Such radiopaque markers 314 may be arranged over the length of the stent 300, as shown. While there are seven separate marker bands 314 illustrated in FIG. 3, it is contemplated that there may be any number of marker bands 314 desired, such as, but not limited to, zero, one, two, three, four, or more. Further, the marker bands 314 positioned at any location on the stent desired. In some instances, the entire stent 300 may be coated with a radiopaque material for accomplishing fluoroscopic positioning. Optionally, the stent 300 may not include any such markers at all.

A retrieval wire 316 may be positioned adjacent to the flared proximal end 306, as shown. The retrieval wire 316 may facilitate removal of the stent 300 once the stapling line has healed. In some embodiments, the retrieval wire 316 may have a hook or latch, which may be able to attach to an elongated device (such as an endoscope) to facilitate removal of the stent 300 by pulling it from the flared proximal end 306 in the proximal direction. Further, the retrieval wire 316 may be made from the same material as the stent frame 302, or of the coating 304, and/or both, and may be integrated into the design of the stent 300 during the stent's manufacture. Alternatively, the retrieval wire 316 may be attachable to the stent 300 through known methods of applying industrial adhesives, welding, soldering, brazing, etc. Removal of the stent through the retrieval wire 316 may be carried out through specific medical instruments that are configured to carry out such operations, and those may be well known to someone skilled in the art.

In the deployed position, the stent frame 302 may extend from a distal portion of the esophagus into the small pouch, bridging the Z line which forms the gastroesophageal junction. Likewise, the flared distal end 308 of the stent frame 302 may span between the gastro jejunal anastomosis and the Roux limb, bridging the small pouch and the Roux limb. In some embodiments, a portion of the stent frame 302 extending from the flared proximal end 306 to the expandable middle segment 312, spanning the esophagus and the small pouch (referred to as length $L_2$) may be about 18 to 22 mm in length and may have a width $W_2$ of about 18 to 22 mm. In some embodiments, a portion of the stent frame 302 extending from the expandable middle segment 312 to the flared distal end 308 (referred to as length $L_4$) may be about 20 to 70 mm in length, depending on the application, and may have a width $W_3$ of about 10 to 14 mm. However, these ranges are merely exemplary. It is contemplated the width/diameter and length of each section may be determined by the desired application and/or placement within the body.

Referring now to FIG. 4, an inflation valve 436 may be positioned to extend between the inner lumen 434, formed through the inner stent wall 432, and an inner portion of the inflatable balloon 312. This may provide a regulated passage for an inflation fluid to travel into the inflatable balloon 312, such that the balloon 312 can be inflated and/or deflated as desired. More particularly, the inflation valve 436 may be any of a number of widely applied valves, applicable in surgeries and medical implants, and may be made from a biocompatible material. In structure, the inflation valve 436 may protrude into the inflatable balloon 312, instead of the inner lumen 434, as shown, where it may inhibit flow of food and liquids.

In some embodiments, the inflation valve 436 may be a unidirectional valve that provides a regulated passage for an amount of air or a suitable fluid into an inner space within the inflatable balloon 312. Operationally, the inflation valve 436 may provide such a passage upon an application of pressure from inside the inner lumen 434, when applied radially outwards. More explicitly, the pressure from the inner lumen 434, into the inflatable balloon, may be initiated through an external medium, such as a catheter lumen or an inflation device that is introduced into the stent 300 for the balloon's inflation.

In further detail, during stent positioning and implantation, an external pressure may be applied to open the inflation valve 436 after the stent 300 is positioned adjacent to a post-anastomosis surgery leak. An elongated device such as a catheter or other inflation device, providing an inflation fluid, may extend through the esophagus and may pass through the stent's inner lumen 434 to reach the inflation valve 436. Once reached, the inflation device may engage the inflation valve 436 and deliver an inflation fluid into the inflatable balloon 312. Once the balloon 312 has been inflated to the desired extent, the inflation device may be disengaged from the inflation valve 436 and retracted from the stent 300.

Deflation of the inflatable balloon may be performed by introducing the inflation device through the esophagus and the stent's inner lumen 434, deploying the inflation device relative to the inflation valve 436, as noted above, and drawing the inflation fluid out through a suction mechanism. A connection or coupling between the inflation device and the inflation valve 436 may be enabled through various types of known connections such as a leur lock connection, latch coupling, magnetic connections, etc. In some embodiments, the inflation device may be introduced through other bodily cavities or through an incision-based opening.

Additionally, the stent 300 may include a valve 438 to prevent reflux of any consumed food, etc., that may travel through the inner lumen 434 of the elongated tube 303. Located within the inner lumen 434, the valve 438 may be any of the widely applied unidirectional valves that are capable of restricting the passage of food to only one direction. Moreover, the valve's placement may be substantially perpendicular to the length of the stent 300. Optionally, the valve 438 may be located in other parts of the stent including the elongated tube adjacent to the flared distal end 308. The placement of the valve 438 may depend upon the patient's digestive system, the surgical process, other anatomical requirements, etc. In effect, the valve 438 may be configured to allow any consumed flow of food, liquid, etc., to flow in the distal direction, while preventing a flow in the reverse or the proximal direction.

In some embodiments, the stent 300 may be coated with a drug, a therapeutic agent, or a medicinal agent, to improve healing at the stapling line. Certain drugs may be applied to eliminate harmful effects of the gastric juices that may be produced within the small pouch over the period of healing. Additionally, absorbent materials may be employed along the external surface of the stent 300, over the coating 304, to absorb those gastric juices as well.

Figure 5:
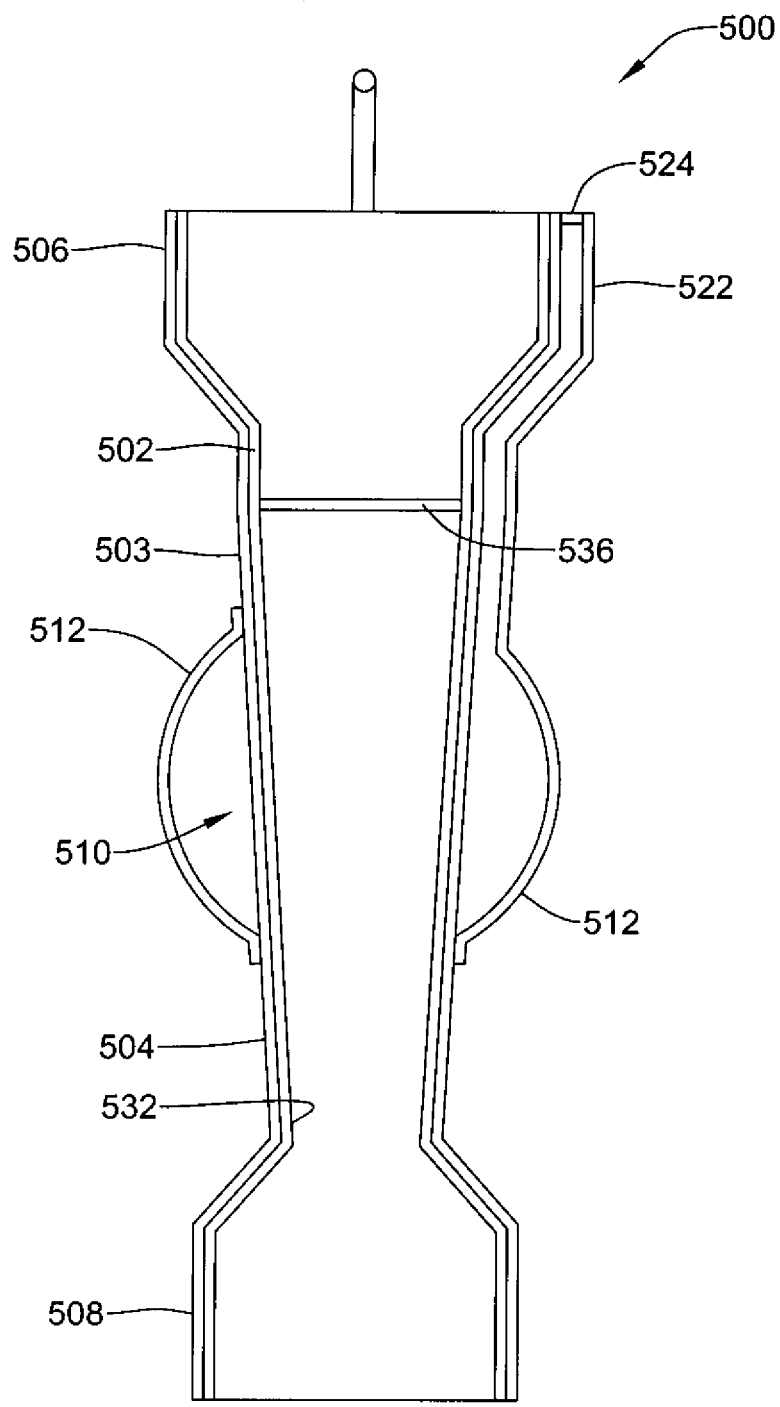
FIG. 5 is a cross-sectional view of another illustrative stent.

Referring now to FIG. 5, another illustrative embodiment of a stent 500 will be described. The stent 500 may include features similar in form and function to the stent 300, discussed in connection with FIGS. 3 and 4. The stent 500 may include a structured stent frame 502, externally coated, and optionally internally coated, with a coating 504 to form an elongated tube. At either end of the stent 500, there may be a flared proximal end 506 and a flared distal end 508. Further, an intermediate region 510 may include an intermediate tubular structure 503 and an inflatable balloon 512. The stent frame 502 may define an inner wall 532, thereby forming an inner lumen 534. In addition, a reflux valve 536, similar to the valve 438 may be provided.

The stent 500 may include an alternate method of inflating or delivering the inflation air/fluid to the inflatable balloon 512, thus expanding the inflatable balloon 512. Accordingly, in some embodiments, an inflation lumen 522 may be structured along the external surface of the elongated tube 503, extending from the flared proximal end 506 of the stent frame 502 to reach a proximal end of the inflatable balloon 512, as shown. The inflation air/fluid from the outside may be delivered into the inflatable balloon 512 through the inflation lumen 522. Here, an inflation device (not shown), adapted to deliver the inflation air/fluid, may pass through the esophagus, and be alternatively affixed to a portion proximal to the stent 500, fluidly communicating with the proximal end of the inflation lumen 522. An amount of inflation air/fluid passing through the inflation device may enter the inflation lumen 522, eventually delivering that amount of inflation air/fluid into the inflatable balloon 512.

In addition, an inflation valve 524, similar to the inflation valve 436 (see FIG. 4), may be operably positioned adjacent the flared proximal end 506 where the inflation device (not shown) fluidly connects with the proximal end of the inflation lumen 522. The inflation valve 524, in particular, may form a coupling interface between the inflation lumen 522 and the inflation device. Similar to the mechanism already discussed, various other connection mechanisms may be used. In some embodiments, the inflation lumen 522 may extend externally, all along the circumference of the elongated tube 503, as well. Those skilled in the art may understandably employ multiple other configurations and variations.

Structural configurations, cross-sectional profiles, embodiments, and sizes of the stent 500, described so far, may vary from application to application. Moreover, other embodiments of the stent 500 may be readily construed and applied without departing from the scope of the present disclosure. The dimensions and structural variations mentioned so far thus need to seen as limiting in any way.

Figure 2:
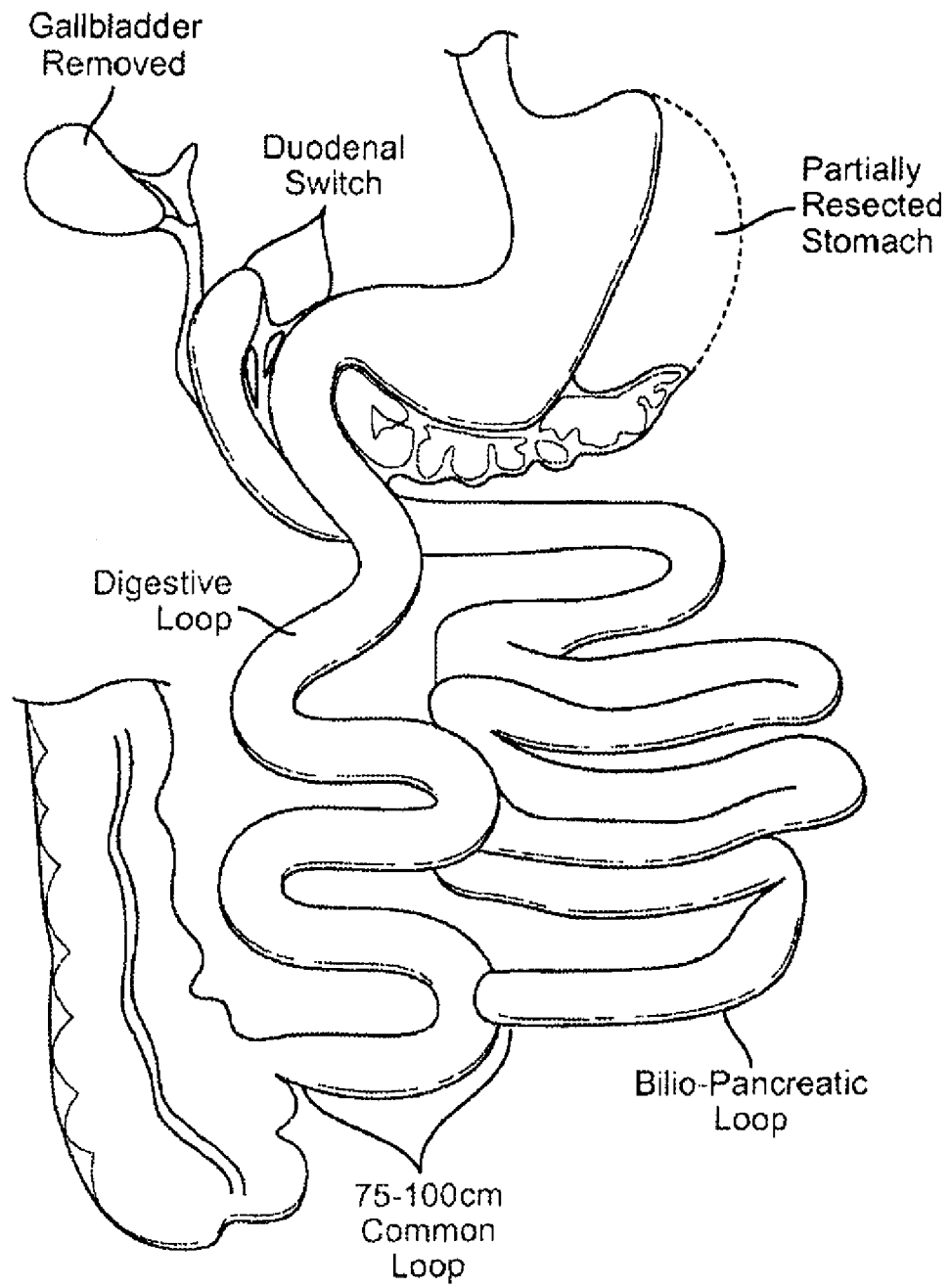
FIG. 2 is a schematic view of portions of an alimentary canal after a biliopancreatic diversion with duodenal switch procedure.

Sleeve gastrectomy is another surgical process, similar to Roux-en-Y, carried out to treat obesity. In general, after a sleeve gastrectomy or a biliopancreatic diversion with duodenal switch, the stomach pouch becomes longer and thinner than before, as shown in FIG. 2, and thus, the stomach may be termed as a sleeve pouch.

Figure 6:
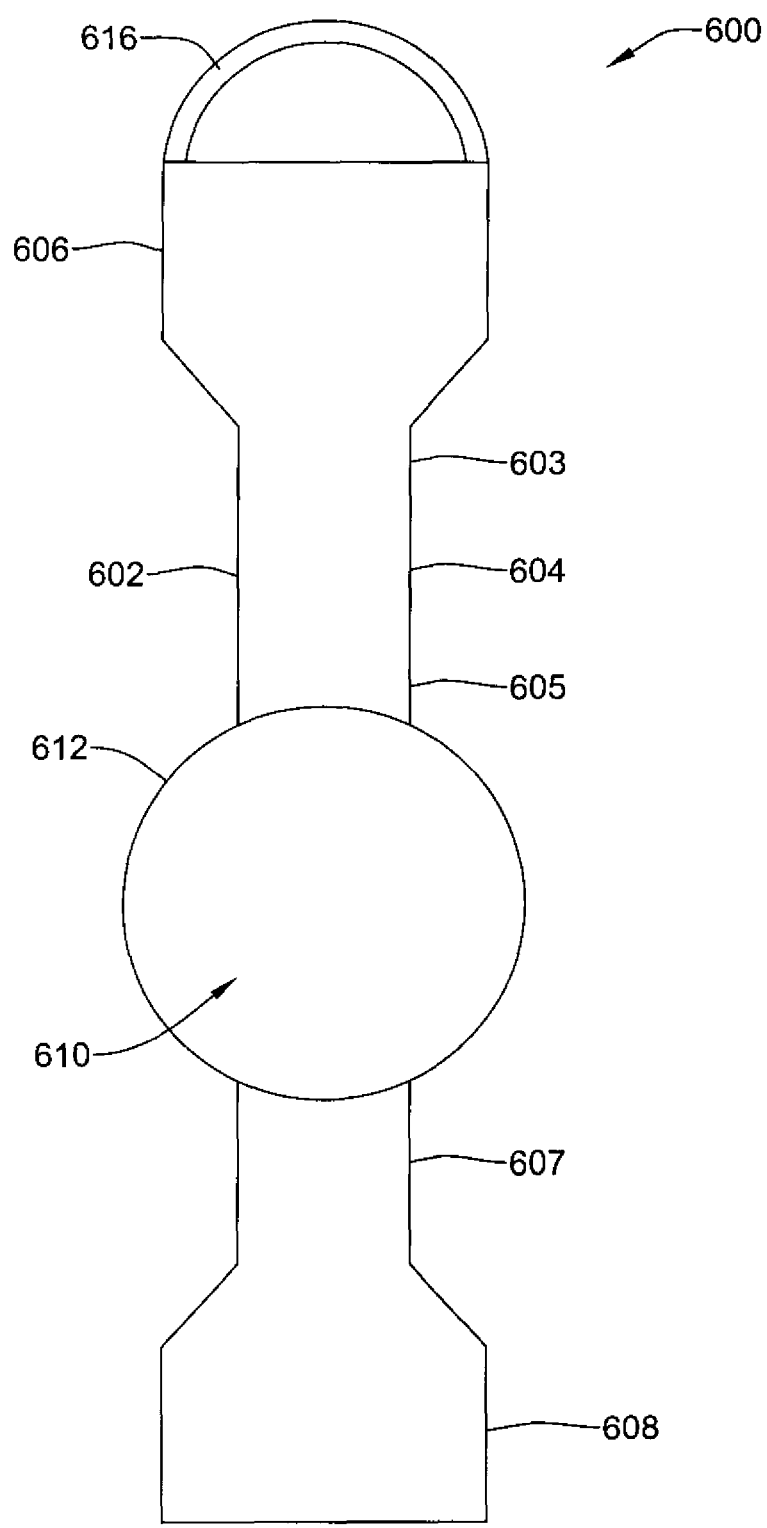
FIG. 6 is a side view of another illustrative stent.

Another illustrative stent 600 is depicted in FIG. 6. In some instances, the stent 600 may include features similar in form and function to the stents 300, 500, discussed above. However, the stent 600 may be sized and structured to accommodate the shape of the stomach following a sleeve gastrectomy. The stent 600 may be configured to temporarily seal leaks occurring at a stapling line after the surgery, and can be removed once those leaks have healed. The stent 600 may include an elongated tubular stent frame 602. The stent frame 602 may have a woven structure, fabricated from a number of filaments. In some embodiments, the stent frame 602 may be braided with one filament. In other embodiments, the stent frame 602 may be braided or knitted with several filaments. In yet another embodiment, the stent frame 602 may be of a knotted type. In still another embodiment, the stent frame 602 may be laser cut.

In some instances, the stent frame 602 may be entirely, substantially or partially, covered with a polymeric coating 604. In some instances, the coating 604 may be disposed over an outer surface of the stent frame 602. In other instances, the coating 604 may be disposed over an inner surface of the stent frame 602 or both the inner and outer surfaces. At either end of the stent 600, there may be a flared proximal end 606 and a flared distal end 608. The flared proximal end 606 and the flared distal end 608 may be configured to contact the corresponding body lumen to prevent passage of food or liquid between the stent 600 and the corresponding lumen wall. Further, an intermediate region 610 disposed between the flared ends 606, 608 may include an intermediate tubular structure 603 and an expandable middle region or inflatable balloon 612. The expandable middle segment 612 may prevent distal/proximal displacement and/or migration of the stent 600, once the stent 600 is positioned and expanded. The stent frame 602 may define an inner wall, thereby forming an inner lumen. While not explicitly shown, a reflux valve, similar to valves 438, 536 and/or radiopaque marker bands may be provided.

As discussed above, the stent 600 may be sized and shaped to better fit the geometry of a sleeve-shaped stomach after a sleeve gastrectomy surgery. For example, the inflatable balloon 612, may be positioned closer to the flared distal end 608. This may form a longer proximal segment 605 configured to be positioned in the sleeve pouch and a shorter distal segment 607. The proximal segment 605 may be configured to extend between a flared proximal end 606 and the inflatable balloon 612 and the distal segment 607 may be configured to extend between the inflatable balloon 612 and a flared distal end 608. In some instances, the proximal segment 605 may have a length of approximately 250-270 mm and a width of approximately 10-20 mm. In some instances, the distal segment 607 may have a length of approximately 60-70 mm and a width of approximately 15-25 mm. However, these ranges are merely exemplary. It is contemplated the width and length of each section may be determined by the desired application and/or placement within the body.

The flared proximal end 606 and flared distal end 608, when in position, may prevent leakage of any food or liquid, etc., into the small pouch. Such sealing may be enabled by sealing the gaps between those ends 606, 608, and the enteral lumen walls. Disposed in a distal region of the esophagus, the flared proximal end 606 may expand along the circumference of the esophagus. The structure at the distal end of the stent 600, that includes the flared distal end 608, may be substantially similar in shape and size to the flared proximal end 606. In some embodiments, the flared distal end 608 may have a different size and shape depending on the size and geometry of the cavity within which it is being placed. Both the flared proximal end 606 and the flared distal end 608 thus form conically enlarged protrusions at their respective ends. In some embodiments, the shape, design, and size, may vary and may include variations such as U-shaped flares, etc., that may be needed depending on surgical and/or anatomical requirements. In some embodiments, the flared proximal end 606 may be approximately 15-25 mm in length and approximately 25-35 mm in cross-sectional diameter at its widest portion. In some embodiments, the flared distal end 608 may be approximately 15-25 mm in length and approximately 25-35 mm in cross-sectional diameter at its widest portion. However, these ranges are merely exemplary. It is contemplated the width and length of each section may be determined by the desired application and/or placement within the body.

To counter such conditions of stent migration, the stent 600 may include an expandable middle segment 612. The expandable middle segment 612 may extend 360° around the elongated tubular section 603, although this is not required. In some embodiments, the expandable middle segment 612 may extend less than 360° around the elongated tubular section 603. The expandable middle segment 612 may be disposed about and secured at the intermediate region 610, and may be positioned within the small pouch until the stapling line is healed. Such an arrangement may help prevent the stent's migration. Moreover, the expandable middle segment 612 may also prevent stagnation and accumulation of food or liquid in the small pouch by filling the small pouch almost entirely.

In some embodiments, the expandable middle segment 612 may be formed from an inflatable balloon. The inflatable balloon 612 may include mechanisms and/or measures to allow a passage of air, saline, or other inflation fluid for performing functions of balloon inflation and deflation, such as those discussed above. In some instances, the inflatable balloon 612 may include, but is not limited to, a substantially spherical or ovoid shape with a cylindrical hole in the center structured for the elongated tube's disposal therethrough. In some embodiments, the inflatable balloon 612 may have an ovoid-shaped with a length that is longer than its width, or vice versa. In some instances, the inflatable balloon 612 may be formed from a compliant, low pressure material, such as, but not limited to, silicone, synthetic polyisoprene, or latex. In other instances, the inflatable balloon 612 may be formed from a high pressure material, such as, but not limited to, polyethylene terephthalate (PET), nylon, polyethylene (PE), polyurethane, or flexible polyvinyl chloride (PVC). Once the stent 600 is positioned within the small pouch, during deployment, the expandable middle segment 612 may be expanded to its desired shape and size. It is contemplated the diameter of the expandable middle segment 612 may be any size desired as determined by the desired application and/or placement within the body. In some instances, the inflatable balloon 612 may have a length of approximately 55 to 65 mm. However, this is just an example. It is contemplated the width and length of each the balloon 612 may be determined by the desired application and/or placement within the body A retrieval wire 616 may be positioned adjacent to the flared proximal end 606, as shown. The retrieval wire 616 may facilitate removal of the stent 600 once the stapling line has healed. In some embodiments, the retrieval wire 616 may have a hook or latch, which may be able to attach to an elongated device (such as an endoscope) to facilitate removal of the stent 600 by pulling it from the flared proximal end 606 in the proximal direction. Further, the retrieval wire 616 may be made from the same material as the stent frame 602, or of the coating 604, and/or both, and may be integrated into the design of the stent 600 during the stent's manufacture. Alternatively, the retrieval wire 616 may be attachable to the stent 600 through known methods of applying industrial adhesives, welding, soldering, brazing, etc. Removal of the stent through the retrieval wire 616 may be carried out through specific medical instruments that are configured to carry out such operations, and those may be well known to someone skilled in the art.

Figure 7:
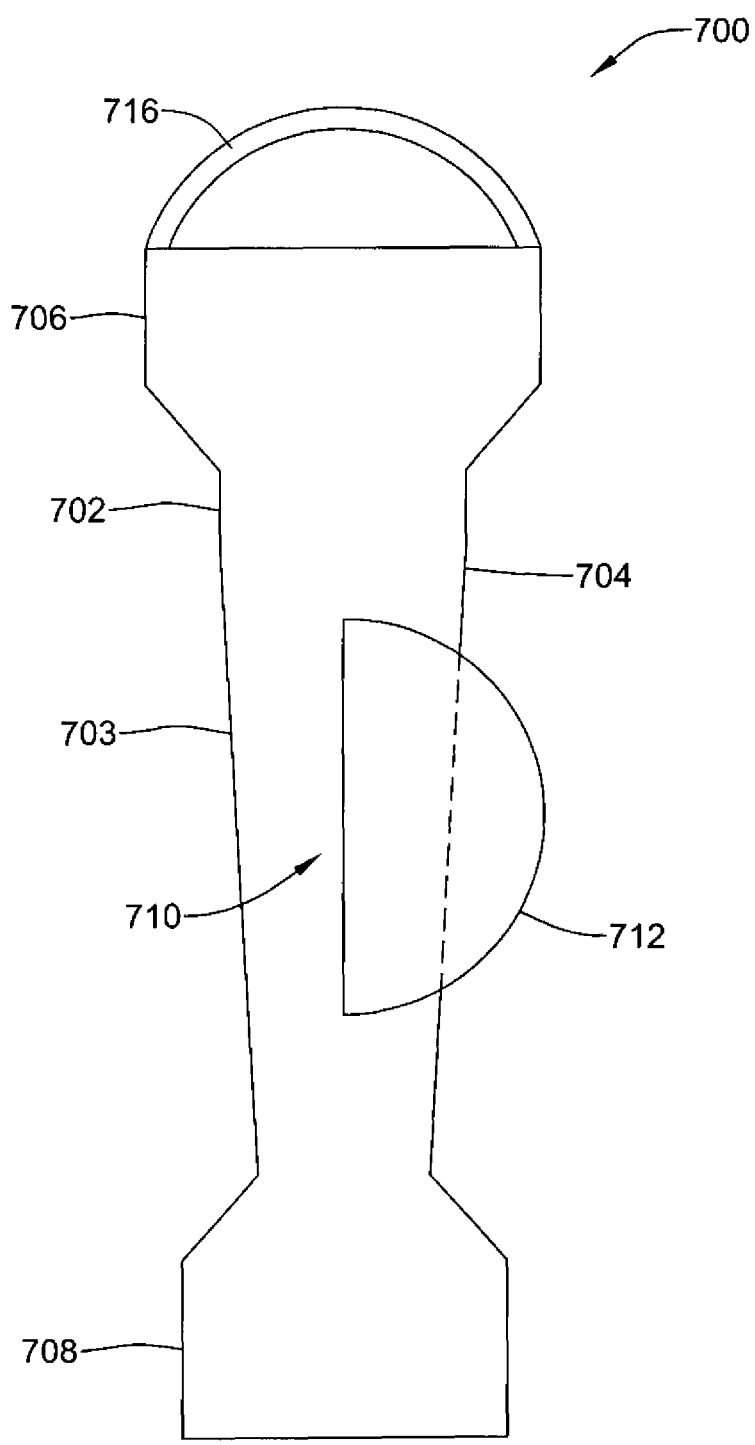
FIG. 7 is a side view of another illustrative stent with a balloon extending less than 360° around the elongated tube.

Another illustrative stent 700 is depicted in FIG. 7. In some instances, the stent 700 may include features similar in form and function to the stents 300, 500, 600 discussed above. The stent 700 may be configured to temporarily seal leaks occurring at a stapling line after the surgery, and can be removed once those leaks have healed. The stent 700 may include an elongated tubular stent frame 702. In some instances, the stent frame 702 may have a woven, knitted, knotted, or braided structure, fabricated from a number of filaments. In other embodiments, the stent frame 702 may be braided with one filament. In still another embodiment, the stent frame 702 may be laser cut.

In some instances, the stent frame 702 may be entirely, substantially or partially, covered with a polymeric coating 704. In some instances, the coating 704 may be disposed over an outer surface of the stent frame 702. In other instances, the coating 704 may be disposed over an inner surface of the stent frame 702 or both the inner and outer surfaces. At either end of the stent 700, there may be a flared proximal end 706 and a flared distal end 708. The flared proximal end 706 and the flared distal end 708 may be configured to contact the corresponding body lumen to prevent passage of food or liquid between the stent 700 and the corresponding lumen wall. Further, an intermediate region 710 disposed between the flared ends 706, 708 may include an intermediate tubular structure 703 and an expandable middle region or inflatable balloon 712. The expandable middle segment 712 may prevent distal/proximal displacement and/or migration of the stent 700, once the stent 700 is positioned and expanded. The stent frame 702 may define an inner wall, thereby forming an inner lumen. While not explicitly shown, a reflux valve, similar to valves 438, 536 and/or radiopaque marker bands may be provided.

The flared proximal end 706 and flared distal end 708, when in position, may prevent leakage of any food or liquid, etc., into the small pouch. Such sealing may be enabled by sealing the gaps between those ends 706, 708, and the enteral lumen walls. Disposed in a distal region of the esophagus, the flared proximal end 706 may expand along the circumference of the esophagus. The structure at the distal end of the stent 700, that includes the flared distal end 708, may be substantially similar in shape and size to the flared proximal end 706. In some embodiments, the flared distal end 708 may have a different size and shape depending on the size and geometry of the cavity within which it is being placed. Both the flared proximal end 706 and the flared distal end 708 thus form conically enlarged protrusions at their respective ends. In some embodiments, the shape, design, and size, may vary and may include variations such as U-shaped flares, etc., that may be needed depending on surgical and/or anatomical requirements.

To counter such conditions of stent migration, the stent 700 may include an expandable middle segment or inflatable balloon 712. As shown, the expandable middle segment 712 may extend less than 360° around the elongated tubular section 703, although this is not required. Accordingly, the expandable middle segment 712 can form shapes that may resemble a half donut, or a quarter donut, etc. Thus, the size and shape of the expandable middle segment 712 may be modified to fit the anatomical requirements and/or restrictions of the patient's body. It is contemplated that the size and shape of the balloon 712 may be selected for custom fit for the desired application. The expandable middle segment 712 may be disposed about and secured at the intermediate region 710, and may be positioned within the small pouch until the stapling line is healed. Such an arrangement may help prevent the stent's migration. Moreover, the expandable middle segment 712 may also prevent stagnation and accumulation of food or liquid in the small pouch by filling the small pouch almost entirely.

In some embodiments, the expandable middle segment 712 may be formed from an inflatable balloon. The inflatable balloon 712 may include mechanisms and/or measures to allow a passage of air, saline, or other inflation fluid for performing functions of balloon inflation and deflation, such as those discussed above. In some instances, the inflatable balloon 712 may be formed from a compliant, low pressure material, such as, but not limited to, silicone, synthetic polyisoprene, or latex. In other instances, the inflatable balloon 712 may be formed from a high pressure material, such as, but not limited to, polyethylene terephthalate (PET), nylon, polyethylene (PE), polyurethane, or flexible polyvinyl chloride (PVC). Once the stent 700 is positioned within the small pouch, during deployment, the expandable middle segment 712 may be expanded to its desired shape and size. It is contemplated the diameter of the expandable middle segment 712 may be any size desired as determined by the desired application and/or placement within the body.

A retrieval wire 716 may be positioned adjacent to the flared proximal end 706, as shown. The retrieval wire 716 may facilitate removal of the stent 700 once the stapling line has healed. In some embodiments, the retrieval wire 716 may have a hook or latch, which may be able to attach to an elongated device (such as an endoscope) to facilitate removal of the stent 700 by pulling it from the flared proximal end 706 in the proximal direction. Further, the retrieval wire 716 may be made from the same material as the stent frame 702, or of the coating 704, and/or both, and may be integrated into the design of the stent 700 during the stent's manufacture. Alternatively, the retrieval wire 716 may be attachable to the stent 700 through known methods of applying industrial adhesives, welding, soldering, brazing, etc. Removal of the stent through the retrieval wire 716 may be carried out through specific medical instruments that are configured to carry out such operations, and those may be well known to someone skilled in the art.

Figure 8:
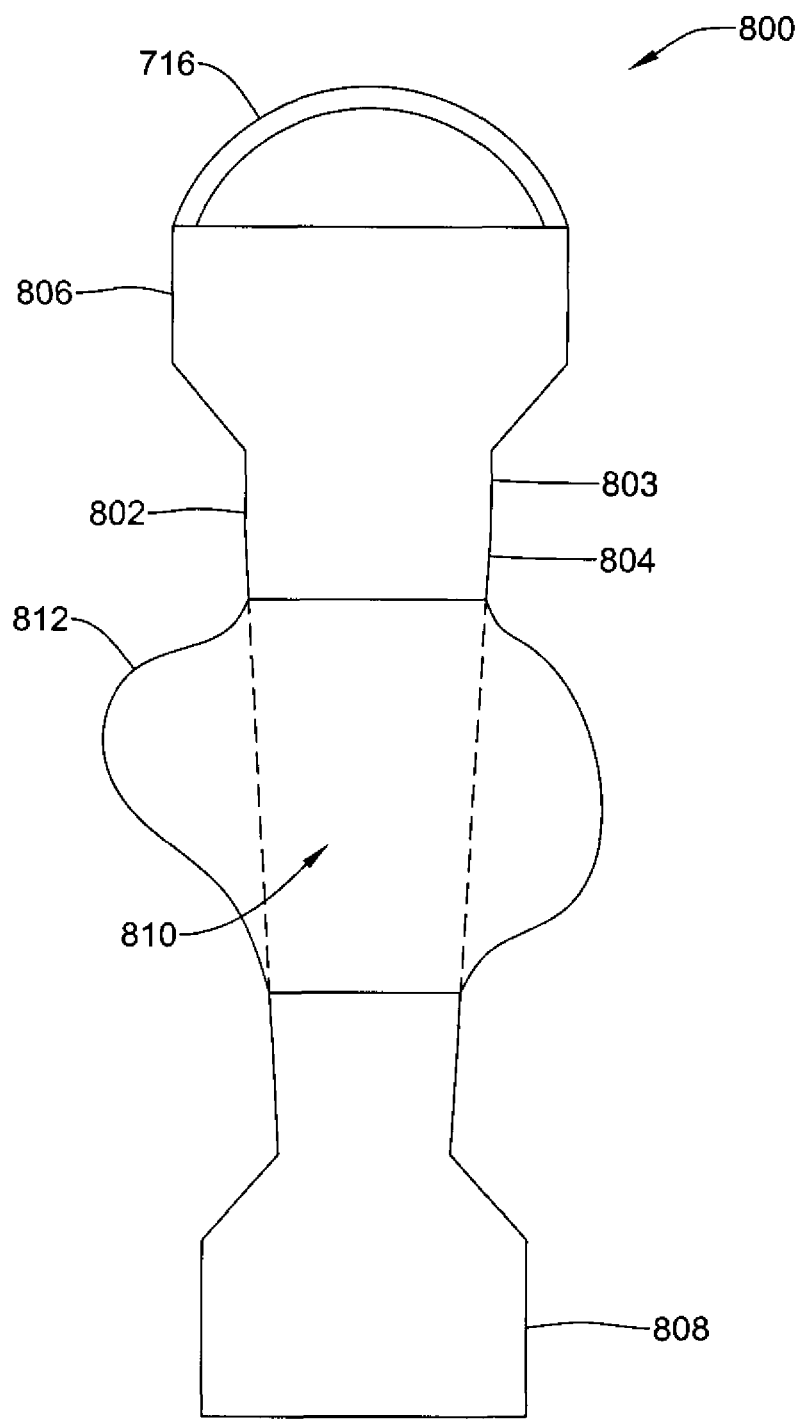
FIG. 8 is a side view of another illustrative stent having a custom shaped balloon.

Another illustrative stent 800 is depicted in FIG. 8. In some instances, the stent 800 may include features similar in form and function to the stents 300, 500, 600, 700 discussed above. The stent 800 may be configured to temporarily seal leaks occurring at a stapling line after the surgery, and can be removed once those leaks have healed. The stent 800 may include an elongated tubular stent frame 802. In some instances, the stent frame 802 may have a woven, knitted, knotted, or braided structure, fabricated from a number of filaments. In other embodiments, the stent frame 802 may be braided with one filament. In still another embodiment, the stent frame 802 may be laser cut.

In some instances, the stent frame 802 may be entirely, substantially or partially, covered with a polymeric coating 804. In some instances, the coating 804 may be disposed over an outer surface of the stent frame 802. In other instances, the coating 804 may be disposed over an inner surface of the stent frame 802 or both the inner and outer surfaces. At either end of the stent 800, there may be a flared proximal end 806 and a flared distal end 808. The flared proximal end 806 and the flared distal end 808 may be configured to contact the corresponding body lumen to prevent passage of food or liquid between the stent 800 and the corresponding lumen wall. Further, an intermediate region 810 disposed between the flared ends 806, 808 may include an intermediate tubular structure 803 and an expandable middle region or inflatable balloon 812. The expandable middle segment 812 may prevent distal/proximal displacement and/or migration of the stent 800, once the stent 800 is positioned and expanded. The stent frame 802 may define an inner wall, thereby forming an inner lumen. While not explicitly shown, a reflux valve, similar to valves 438, 536 and/or radiopaque marker bands may be provided.

The flared proximal end 806 and flared distal end 808, when in position, may prevent leakage of any food or liquid, etc., into the small pouch. Such sealing may be enabled by sealing the gaps between those ends 806, 808, and the enteral lumen walls. Disposed in a distal region of the esophagus, the flared proximal end 806 may expand along the circumference of the esophagus. The structure at the distal end of the stent 800, that includes the flared distal end 808, may be substantially similar in shape and size to the flared proximal end 806. In some embodiments, the flared distal end 808 may have a different size and shape depending on the size and geometry of the cavity within which it is being placed. Both the flared proximal end 806 and the flared distal end 808 thus form conically enlarged protrusions at their respective ends. In some embodiments, the shape, design, and size, may vary and may include variations such as U-shaped flares, etc., that may be needed depending on surgical and/or anatomical requirements.

To counter such conditions of stent migration, the stent 800 may include an expandable middle segment or inflatable balloon 812. The expandable middle segment 812 may extend 360° around the elongated tubular section 803, although this is not required. In some embodiments, the expandable middle segment 812 may extend less than 360° around the elongated tubular section 803. It is contemplated that the size and shape of the balloon 812 may be selected for custom fit for the desired application. For example, the shape of the middle segment 812 may be chosen to match the anatomical requirements of the patient or other requirements of the surgery. Accordingly, the structure of the middle segment 812 may be irregular and may not take the form of a typical geometric shape such as sphere, ovoid, etc. The expandable middle segment 812 may be disposed about and secured at the intermediate region 810, and may be positioned within the small pouch until the stapling line is healed. Such an arrangement may help prevent the stent's migration. Moreover, the expandable middle segment 812 may also prevent stagnation and accumulation of food or liquid in the small pouch by filling the small pouch almost entirely.

In some embodiments, the expandable middle segment 812 may be formed from an inflatable balloon. The inflatable balloon 812 may include mechanisms and/or measures to allow a passage of air, saline, or other inflation fluid for performing functions of balloon inflation and deflation, such as those discussed above. In some instances, the inflatable balloon 812 may be formed from a compliant, low pressure material, such as, but not limited to, silicone, synthetic polyisoprene, or latex. In other instances, the inflatable balloon 812 may be formed from a high pressure material, such as, but not limited to, polyethylene terephthalate (PET), nylon, polyethylene (PE), polyurethane, or flexible polyvinyl chloride (PVC). Once the stent 800 is positioned within the small pouch, during deployment, the expandable middle segment 812 may be expanded to its desired shape and size. It is contemplated the diameter of the expandable middle segment 812 may be any size desired as determined by the desired application and/or placement within the body.

A retrieval wire 816 may be positioned adjacent to the flared proximal end 806, as shown. The retrieval wire 816 may facilitate removal of the stent 800 once the stapling line has healed. In some embodiments, the retrieval wire 816 may have a hook or latch, which may be able to attach to an elongated device (such as an endoscope) to facilitate removal of the stent 800 by pulling it from the flared proximal end 806 in the proximal direction. Further, the retrieval wire 816 may be made from the same material as the stent frame 802, or of the coating 804, and/or both, and may be integrated into the design of the stent 800 during the stent's manufacture. Alternatively, the retrieval wire 816 may be attachable to the stent 800 through known methods of applying industrial adhesives, welding, soldering, brazing, etc. Removal of the stent through the retrieval wire 816 may be carried out through specific medical instruments that are configured to carry out such operations, and those may be well known to someone skilled in the art.

During implantation, the stent may be implanted through endoscopic procedures, and therefore, they may be mounted on a delivery device for delivery under direct vision and/or under fluoroscopy. Accordingly, the method of repairing post-anastomosis surgery leaks is discussed infra.

Operationally, an operator may provide at least one of the stents disclosed so far, and may mount it over an elongated device (not shown), which is configured to deliver and implant such stents to a target site. Here, the elongated device may include, but not limited to, an inflatable balloon, a mechanically expandable apparatus, such as the ones that function like expandable mandrels, etc. The operator may thereafter insert and advance the stent mounted on the elongated device through a body lumen or an alimentary canal to position the stent adjacent a leak. After positioning the stent adjacent the desired treatment location, the operator may inflate or expand the inflatable balloon, or the mechanically expandable apparatus, disposed on the elongated device, to an appropriate extent, thereby expanding the stent mounted on it. Such expansion may allow the stent to abut against the enteral wall of the esophagus and the proximal end of the Roux limb, limiting any form of leak thereof. Next, the operator expands the corresponding expandable middle segment, or inflates it when employed with an inflatable balloon, filling the small pouch or the sleeve pouch almost entirely with the expandable middle segment. Radiopaque markers, similar to the radiopaque markers 314 (see FIG. 3), may enable an operator to ascertain whether the expansion is desirable, optimal, and safe. Finally, once the stent is positioned, the operator may deflate, retract, and/or remove, the elongated device through the esophagus.

The materials that can be used for the various components of stent 300 (and/or other medical devices disclosed herein) may include those commonly associated with medical devices. For simplicity purposes, the following discussion makes reference to stent 300. However, this is not intended to limit the devices and methods described herein, as the discussion may be applied to other similar medical devices disclosed herein.

Stent 300 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of stent 300 may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of stent 300 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of stent 300 to achieve the same result.

In some embodiments, a degree of Magnetic Resonance Imaging (MRI) compatibility is imparted into stent 300. For example, stent 300 or portions thereof, may be made of a material that does not substantially distort the image and create substantial artifacts (i.e., gaps in the image). Certain ferromagnetic materials, for example, may not be suitable because they may create artifacts in an MRI image. Stent 300 or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers for stent 300 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will appreciate that the different embodiments of the stent described here, their mode of operation, etc., are merely representative of the environment in which the present disclosure operates. Accordingly, a variety of alternatively shaped collaborating components may also be used as a substitutive for the purpose of engaging, steering and locating the stent at a desired target site, thus, not limiting the scope of the present disclosure. Further, the disclosed stents, along with its middle segment disposed approximately at the stent's the intermediate region, may be adequately stretchable, extendable, and retractable, allowing for its flexible deployment. More particularly, the configurations described here may be applicable for other medical applications as well, and accordingly, a variety of other medical devices may be used in combination with the stent. Those medical equipments may include biopsy forceps, scissors, lithotripters, dilators, other cautery tools, and the like.

Further, while the stent is generally described along with an exemplary intermediate region, providing the stent with an expandable middle segment, along with other embodiments, a variety of other configurations and arrangements may also be contemplated and conceived as well. In addition, the operations, devices, and components, described herein may be equally applicable for other purposes where a component is required to be positioned in places where a leakage needs to be avoided. Embodiments of the present disclosure are thus applicable to medical and/or non-medical environments. Further, certain aspects of the aforementioned embodiments may be selectively used in collaboration, or removed, during practice, without departing from the scope of the disclosed embodiments.

Those skilled in the art will recognize that the present invention may be manifested in a variety of forms other than the specific embodiments described and contemplated herein. Accordingly, departure in form and detail may be made without departing from the scope and spirit of the present disclosure as described in the appended claims.

What is claimed is:

1. A stent, comprising:
an elongated tube having a flared proximal end having a first width, a flared distal end having a fourth width, and an intermediate region disposed therebetween, wherein the intermediate region tapers distally from a second width distal of the flared proximal end to a third width proximal of the flared distal end, wherein the second width is larger than the third width and wherein the first width is larger than the fourth width;
an anti-reflux valve disposed within the elongated tube;
a covering disposed over the elongated tube;
an inflatable balloon extending 360° around an exterior of the intermediate region, the inflatable balloon having an inflated center diameter that is larger than the fourth width;
an inflation valve positioned between an inner lumen of the elongated tube and the balloon, the inflation valve positioned within the balloon between proximal and distal ends of the balloon; and
a retrieval wire extending from the flared proximal end.

2. The stent of claim 1, wherein the elongated tube is woven, braided or knitted.

3. The stent of claim 1, wherein the balloon is formed from a compliant material.

4. The stent of claim 1, further comprising at least one radiopaque marker band.

5. The stent of claim 1, wherein the anti-reflux valve is positioned perpendicular to a longitudinal axis of the elongated tube.

6. The stent of claim 1, wherein the inflatable balloon has an inflated outermost diameter that is substantially the same as the first width.

7. The stent of claim 1, wherein the flared proximal end includes a cylindrical portion extending to a proximal extremity of the elongated tube and a tapered portion positioned between the cylindrical portion and the intermediate region.

8. The stent of claim 7, wherein the flared distal end includes a cylindrical portion extending to a distal extremity of the elongated tube and a tapered portion positioned between the cylindrical portion of the flared distal end and the intermediate region.

9. The stent of claim 1, wherein the inflatable balloon is spherical.

10. The stent of claim 1, wherein the flared distal end extends distal beyond the inflatable balloon.

11. A stent, comprising:
an elongated tube having a flared proximal end region, a flared distal end region, and an intermediate region extending between the proximal end region and the distal end region, wherein the intermediate region tapers distally from a first width distal of the flared proximal end region to a second width proximal of the flared distal end region, wherein the first width is larger than the second width;

an anti-reflux valve disposed within the elongated tube;

a polymeric covering disposed over the elongated tube; and an inflatable balloon secured to and extending 360° around an exterior of the intermediate region, the inflatable balloon including an inflation valve extending between an inner surface of the elongated tube and an inner portion of the inflatable balloon, the inflation valve positioned within the balloon between proximal and distal ends of the balloon, the inflation valve configured to inflate and deflate the balloon.

12. The stent of claim 11, wherein the polymeric covering comprises a silicone, styrene isoprene butadiene, expanded polytetrafluoroethylene, or polyurethane.

13. The stent of claim 11, wherein the inflatable balloon has an inflated outermost diameter that is substantially the same as a width of the flared proximal end region.

14. The stent of claim 11, wherein:

the flared proximal end region includes a cylindrical portion extending to a proximal extremity of the elongated tube and a tapered portion positioned between the cylindrical portion and the intermediate region; and the flared distal end region includes a cylindrical portion extending to a distal extremity of the elongated tube and a tapered portion positioned between the cylindrical portion of the flared distal end and the intermediate region.

15. A stent, comprising:

an elongated tube having a flared proximal end and a flared distal end and a tapered intermediate region disposed therebetween, wherein the tapered intermediate region tapers distally from a first width distal of the flared proximal end to a second width proximal of the flared distal end, wherein the first width is larger than the second width;

an anti-reflux valve disposed within the elongated tube, the anti-reflux valve disposed perpendicular to a longitudinal axis of the elongated tube;

a covering disposed over the elongated tube;

an inflatable balloon disposed circumferentially around an exterior of the intermediate region; and an inflation valve configured to inflate and deflate the balloon, the inflation valve positioned between an inner lumen of the elongated tube and the balloon, the inflation valve positioned within the balloon between proximal and distal ends of the balloon.

16. The stent of claim 15, wherein the anti-reflux valve is adjacent the flared proximal end.

\* \* \* \* \*